United States Patent [19]

Dubois et al.

[11] Patent Number: 4,717,757

[45] Date of Patent: Jan. 5, 1988

[54] MESOMORPHIC SIDE-CHAIN POLYMERS HAVING HIGH DIELECTRIC ANISOTROPY AND A METHOD FOR PRODUCING SAID POLYMERS

[75] Inventors: Jean C. Dubois, St. Remy Les Chevreuses; Gilles Ravaux, Les Ulis; Pierre Le Barny, Orsauy, all of France

[73] Assignee: Thomson-CSF, Paris, France

[21] Appl. No.: 29,143

[22] Filed: Mar. 23, 1987

[30] Foreign Application Priority Data

Mar. 25, 1986 [FR] France .................. 86 04285

[51] Int. Cl.$^4$ ............................................. C08F 18/20
[52] U.S. Cl. ................................................... 526/246
[58] Field of Search ........................................ 526/246

[56] References Cited

U.S. PATENT DOCUMENTS 4,293,435 10/1981 Portugall et al. .................. 526/321
4,617,371 10/1986 Blumstein et al. .................. 528/194
4,661,576 4/1987 Decobert et al. .................... 526/298

Primary Examiner—Joseph L. Schofer
Assistant Examiner—N. Sarofim
Attorney, Agent, or Firm—Oblon, Fisher, Spivak, McClelland, & Maier

[57] ABSTRACT

The invention relates to a family of sidechain homopolymers of the polyacrylate type derived from 3-fluoro-4-cyanophenol and exhibiting a mesophase of the nematic or smectic-A type. The polymer in accordance with the invention corresponds to the following general chemical formula:

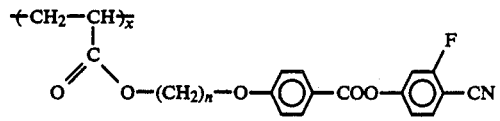

where x indicates the degree of polymerization and $4 \leq n \leq 15$.

1 Claim, 4 Drawing Figures

FIG_1

| n | POLYMERISATION CONDITIONS | | | |
|---|---|---|---|---|
| | SOLVENT | $\frac{M}{A}$ | T(°C) | t (h) |
| 3 | $C_6H_6$ | 30 | 60 | 20 |
| 4 | $C_6H_6$ | 30 | 60 | 93 |
| 6 | THF | 30 | 60 | 24 |
| 11 | THF | 30 | 60 | 21 |

FIG_2

| n | G | SA | N | | L |
|---|---|---|---|---|---|
| 3 | X | 50 | | | X |
| 4 | X | 37 | X | 78,5 | X |
| 6 | X | 16,8 | X | 69,5 | X |
| 11 | X | 1 | X | 69 | X |

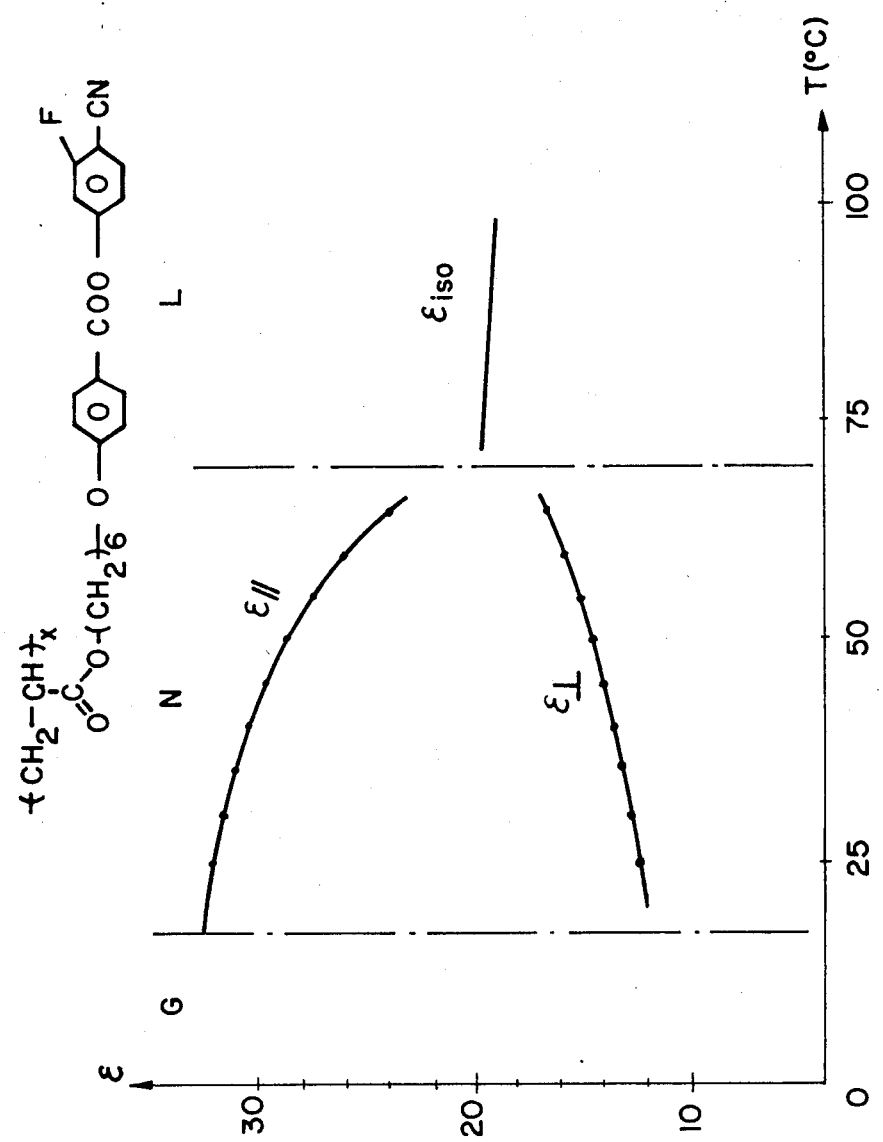
FIG_3

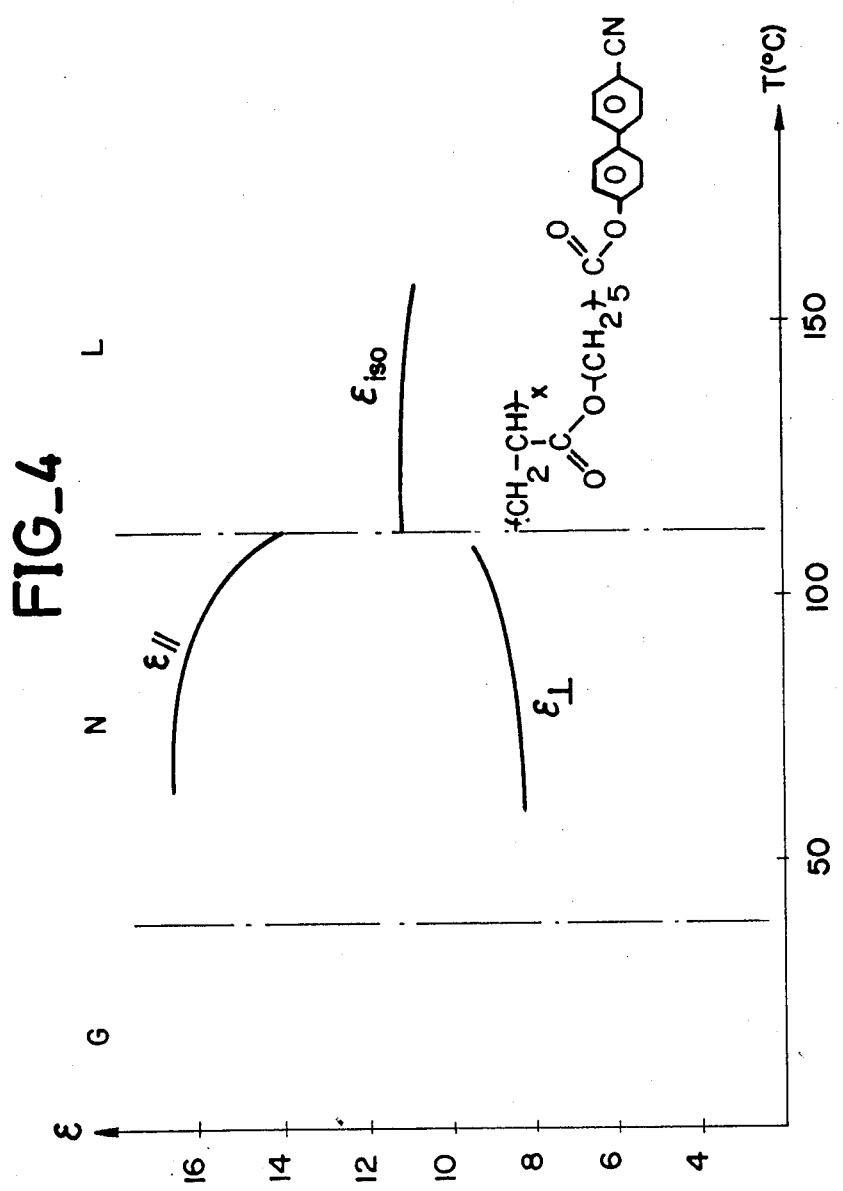

MESOMORPHIC SIDE-CHAIN POLYMERS HAVING HIGH DIELECTRIC ANISOTROPY AND A METHOD FOR PRODUCING SAID POLYMERS

BACKGROUND OF THE INVENTION

1. Field of the Invention

This invention relates to a family of side-chain homopolymers of the polyacrylate type derived from 3-fluoro-4-cyanophenol and exhibiting a mesophase of the nematic or smectic-A type.

2. Description of the Prior Art

At the present time, polymeric materials are being increasingly considered for use in devices developed in such fields as nonlinear optics or visual display. The use of these polymers in display devices is subject to two conditions: they must have high dielectric anisotropy and also a nematic or smectic-A mesophase. There are apparently no known polymers at present in existence which exhibit both these characteristics at the same time.

SUMMARY OF THE INVENTION

In order to overcome these disadvantages, the invention proposes a family of homopolymers which exhibit both high anisotropy (on the order of 20 at room temperature) and a nematic or smectic-A mesophase. The combination of these two characteristics is obtained by introducing in the basic molecule of the polymer a fluorine atom in the ortho position of a cyano group.

One object of the invention is therefore to provide a mesomorphic side-chain polymer which exhibits high dielectric anisotropy and which is distinguished by the fact that the polymer corresponds to the following general chemical formula:

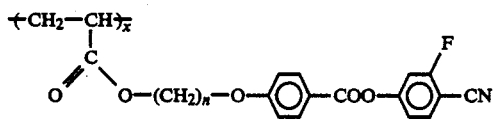

where x indicates the degree of polymerization and $4 \leq n \leq 15$.

A further object of the invention is to provide a method for producing a mesomorphic polymer in accordance with the chemical formula given above, said method being distinguished by the following process steps when $5 \leq n \leq 15$:

First step: obtainment of ω-bromoalkanol by reduction of the corresponding ω-bromoalkanoic acid by means of lithium and aluminum hydride in ether.

Second step: synthesis of 4-(ω-hydroxyalkyloxy)benzoic acid by action of ω-bromoalkanol on 4-hydroxybenzoic acid in a water-alcohol potassium medium.

Third step: obtainment of 4-(acryloyloxyalkyloxy)benzoic acid by esterification of the acid obtained on completion of the second step by means of acrylic acid.

Fourth step: synthesis of 4-(acryloyloxyalkyloxy)benzoyl chloride by means of oxalyl chloride with dimethyl formamide as catalyst.

Fifth step: obtainment of 4-[4'-(acryloyloxyalkyloxy)benzoyloxy]-1-cyano-2-fluorobenzene by action of the chloride obtained on completion of the fourth step on 4-cyano-3-fluorophenol in tetrahydrofuran in the presence of triethylamine.

Sixth step: polymerization of the monomer obtained on completion of the fifth step.

Yet another object of the invention is to provide a method for producing a mesomorphic polymer in accordance with the same chemical formula, this method being distinguished by the following process steps when $n=4$:

First step: protection of the acid function of 4-hydroxybenzoic acid by action of methanol.

Second step: etherification of the product obtained on completion of the first step by action of 1,4-dibromobutane.

Third step: deprotection of the acid function of the product obtained on completion of the second step by reaction in an alcohol potassium medium and then in an acid medium.

Fourth step: esterification of the product obtained on completion of the third step by lithium acrylate in hexamethylphosphoramide.

Fifth step: synthesis of 4-(acryloyloxybutyloxy) benzoyl chloride by action of oxalyl chloride on the product obtained on completion of the fourth step and with dimethyl formamide as catalyst.

Sixth step: obtainment of 4-[4'-(acryloyloxyalkyloxy)benzoyloxy]-1-cyano-2-fluorobenzene by action of the chloride obtained on completion of the fifth step on 4-cyano-3-fluorophenol in tetrahydrofuran in the presence of triethylamine.

Seventh step: polymerization of the monomer obtained on completion of the sixth step.

BRIEF DESCRIPTION OF THE DRAWINGS

FIG. 1 is an explanatory table of polymerization conditions.

FIG. 2 is a table which presents phase transitions of polymers in accordance with the invention.

FIG. 3 is a diagram representing the variation of the dielectric constant of a polymer in accordance with the invention.

FIG. 4 is a diagram representing the variation of the dielectric constant of a polymer in accordance with the prior art.

DESCRIPTION OF THE PREFERRED EMBODIMENTS

The description which follows hereafter will relate to the general method of synthesis of the polymers in accordance with the invention and also to the physical characterizations of these polymers.

General Synthesis Process

The polymers in accordance with the invention are generally obtained in six steps from the following commercial products: ω-bromoalkanoic acid, 4-hydroxybenzoic acid, acrylic acid and 3-fluoro-4-cyanophenol, the synthesis of which is described by S. M. Kelly in the review entitled Helvetica Chimica Acta, vol. 67, 1984, pp. 1572–1579.

Reaction 1: Obtainment of ω-bromoalkanol.

This alcohol is obtained by reduction of the corresponding ω-bromoalkanoic acid by means of lithium and aluminum hydride in ether.

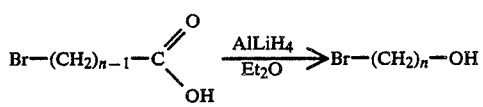

Reaction 2: Synthesis of 4(ω-hydroxyalkyloxy) benzoic acid.

This acid results from the action of ω-bromoalkanol obtained on completion of Reaction 1 on 4-hydroxybenzoic acid in a water-alcohol potassium medium.

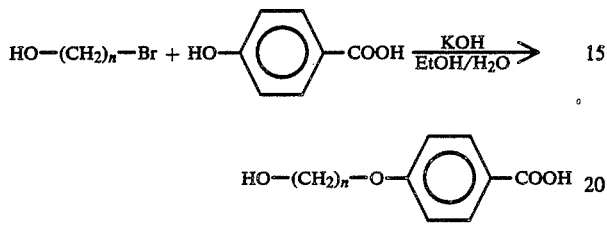

Reaction 3: Obtainment of 4(acryloyloxyalkyloxy)-benzoic acid

Esterification of the 4(ω-hydroxyalkyloxy) benzoic acid obtained on completion of Reaction 2 by means of acrylic acid yields 4(acryloyloxyalkyloxy) benzoic acid. This esterification is performed by utilizing benzene as solvent and para-toluenesulfonic acid (PTSA) as catalyst. During the course of the reaction, hydroquinone is employed as polymerization inhibitor.

$CH_2=CH-COOH\ +$

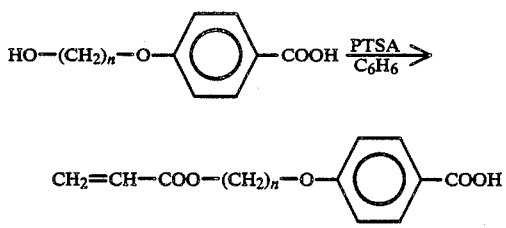

Reaction 4: Synthesis of 4-(acryloyloxyalkyloxy)-benzoyl chloride.

Conversion of the acid obtained on completion of Reaction 3 to acid chloride is performed in the cold state by means of oxalyl chloride by utilizing dimethylformamide (DMF) as catalyst.

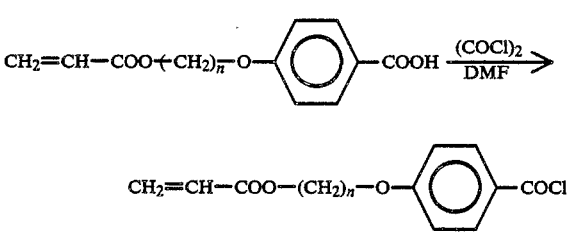

The use of oxalyl chloride instead of thionyl chloride for preparing the desired acid chloride makes it possible to retain the acrylate function.

Reaction 5: Obtainment of 4-[4'-(acryloyloxialkyloxy)benzoylox]-1-cyano-2-fluorobenzene.

This ester is synthesized by action of 4-(acryloyloxyalkyloxy)benzoyl chloride obtained on completion of Reaction 4 on 4-cyano-3-fluorophenol in tetrahydrofuran (THF) in the presence of triethylamine $(C_2H_5)_3N$.

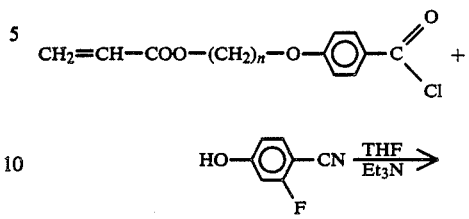

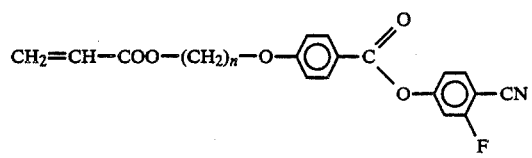

It should be noted that Reaction 2 is not possible in the case of n=4. In a basic medium, 4-bromo1-1-butanol is in fact cyclized in accordance with the following reaction:

In order to obtain 4-[4'-acryloyloxybutyloxy]benzoic acid (that is to say the final product corresponding to Reaction 3 in the general synthesis process, the reaction diagram given below must be adopted.

Protection of the acid function of 4-hydroxybenzoic acid:

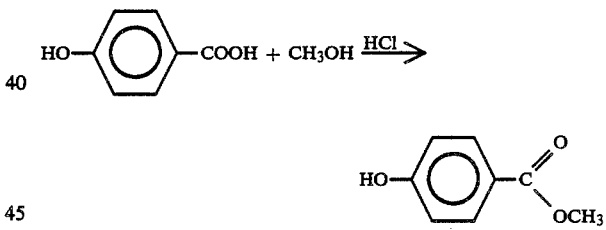

Etherification by means of 1,4-dibromobutane:

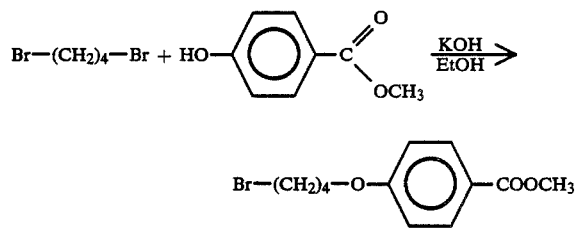

Deprotection of the acid function: This reaction takes place first in an alcohol potassium medium, then in an acid medium.

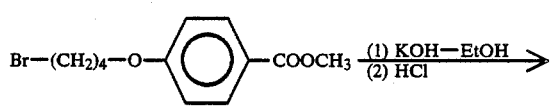

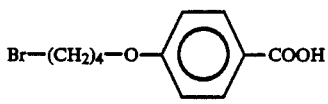

Esterification with lithium acrylate in hexamethylphosphoramide (HMPA).

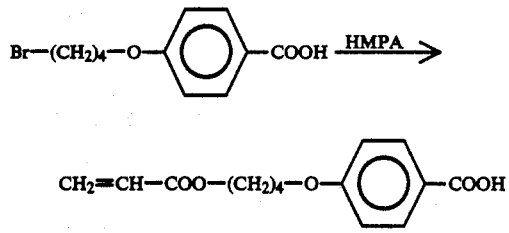

It is therefore apparent that, when n=4, Reactions 1 to 3 of the general synthesis process are replaced by the four reactions given above.

Reaction 6: Polymerization of the monomers.

Polymerization may be performed in vacuum by making use of azobisisobutyronitrile as a free-radical initiator.

Reactions 2 and 3 are described in German patent Application No. DE 3,211,400. The other reactions considered separately are conventional.

The polymers obtained correspond to the following names:

poly [4(4'-acryloyloxybutyloxybenzoyloxy)-4''-cyano-3-fluorophenyl]

poly [4(4'-acryloyloxypentyloxybenzoyloxy)-4''-cyano-3-fluorophenyl]

poly [4(4'-acryloyloxyhexyloxybenzoyloxy)-4''-cyano-3-fluorophenyl]

poly [4(4'-acryloyloxyheptyloxybenzoyloxy)-4''-cyano-3-fluorophenyl]

poly [4(4'-acryloyloxyoctyloxybenzoyloxy)-4''-cyano-3-fluorophenyl]

poly [4(4'-acryloyloxynonyloxybenzoyloxy)-4''-cyano-3-fluorophenyl]

poly [4(4'-acryloyloxydecyloxybenzoyloxy)-4''-cyano-3-fluorophenyl]

poly [4(4'-acryloyloxyundecyloxybenzoyloxy)-4''-cyano-3-fluorophenyl]

poly [4(4'-acryloyloxydodecyloxy-benzoyloxy-4''-cyano-3-fluorophenyl]

poly [4(4'-acryloyloxytridecyloxybenzoyloxy)-4''-cyano-3-fluorophenyl]

poly [4(4'-acryloyloxytetradecyloxybenzoyloxy)-4''-cyano-3-fluorophenyl]

poly [4(4'-acryloyloxypentadecyloxybenzoyloxy)-4''-cyano-3-fluorophenyl]

By way of example, a few conditions of polymerization are grouped together in the table of FIG. 1. This table indicates the nature of the solvent employed, the ratio M/A (where M is the number of moles of the monomer and A is the number of moles of the free-radical initiator), the temperature T in degrees Celsius and the time t in hours. The polymerizations were performed in respect of a few values of n as indicated in the table of FIG. 1.

Physical Properties of the Polymers

In order to obtain a precise definition of their mesomorphic properties, the polymers have been studied by differential enthalpimetric analysis, optical microscopy and x-ray diffraction analysis.

By way of non-limitative example, the results obtained in respect of different values of n are grouped together in the table of FIG. 2. In this table, the letters G, SA, N and L designate respectively the glass transition phase, the smectic-A phase, the nematic phase and the liquid phase. The crosses beneath these letters each indicate a transition from one phase to another. The transition temperatures indicated in this table are expressed in degrees Celsius. It is pointed out that the mesomorphic properties appear only when $n \geq 4$. In fact, when n=3, there exists only one transition (at 50° C.) directly from the glass phase to the liquid phase. The other polymers in accordance with the invention exhibit a nematic phase or a smectic-A phase. The nematic phase extends over 41.5° C. when n=4 and over 52.7° C. when n=6. The smectic-A phase extends over 68° C. when n=11.

The dielectric properties of the polymers in accordance with the invention are particularly advantageous. By way of example, FIG. 3 shows the value of the dielectric constants measured as a function of temperature in respect of an electric field parallel to the optical axis ($\epsilon \parallel$) and in respect of an electric field perpendicular to the optical axis ($\epsilon \perp$). The curves of FIG. 3 have been plotted in respect of n=6. The diagram of FIG. 3 is divided into three zones by straight lines extending vertically from the axis of temperatures. These zones correspond to different phases of the polymer, the transition temperatures of which are listed in the table of FIG. 2. Thus two convergent curves are found to exist in the nematic phase when the temperature rises. The dielectric anisotropy $\Delta \epsilon = \epsilon \parallel - \epsilon \perp$ is positive and its value at 25° C. is 19.6. It is apparent that, in the liquid phase, there remains only a single curve corresponding to the isotropic dielectric constant.

The diagram of FIG. 4 represents the variation of the dielectric constant with temperature in the case of a nematic polymer of the prior art. The polymer considered is a polyacrylate derived from cyanobiphenyl, the chemical formula of which is indicated in the figure. The curves have been plotted from values $\epsilon(\nu)$ extrapolated to zero frequency. This polymer has three phases: glassy, nematic and liquid. The nematic range of this compound is considerable (approximately 70.3° C.). The highest dielectric anisotropy that can be read from this diagram is on the order of 8.2 at 70° C., namely 2.4 times lower than the value indicated earlier in the case of the compound in accordance with the invention (19.6 at 25° C.).

It is apparent that the introduction of a fluorine atom in the ortho position of the cyano group has the effect of reducing the degree of association between the adjacent side-chains of the macromolecules and consequently of increasing the dielectric anisotropy. This explains the value of 19.6 measured at 25° C.

The polymers in accordance with the invention which have a glass transition temperature below the ambient temperature (n=6 or 11, for example) could advantageously be employed in the so-called "guest-host" display devices of the nematic type or of the smectic-A type. Their high dielectric anisotropy in fact permits a reduction in the threshold voltage of the device since this latter is inversely proportional to $\sqrt{\Delta\epsilon}$.

The polymers in accordance with the invention which have a glass transition temperature above the ambient temperature (n=4, for example) find a potential application in nonlinear optics and more specifically in the field of second-harmonic generation. They can in fact serve as an orientation matrix for small molecules having strong second-order hyperpolarizability. By virtue of their lower degree of association in the side chains, these polymers can lead to non-centrosymmetric systems after orientation in an electric field more readily than the cyano polymers.

What is claimed is:

1. A mesomorphic side-chain polymer which exhibits high dielectric anisotropy and corresponds to the following chemical formula:

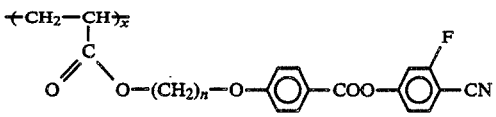

where x indicates the degree of polymerization and $4 \leq n \leq 15$.

* * * * *